United States Patent [19]
Koch et al.

[11] Patent Number: 5,462,715
[45] Date of Patent: Oct. 31, 1995

[54] CUVETTE CONVEYOR

[75] Inventors: Bruno Koch, Cham; Gottlieb Schacher, Ebikon, both of Switzerland

[73] Assignee: Hoffmann-La Roche Inc., Nutley, N.J.

[21] Appl. No.: 286,892

[22] Filed: Aug. 8, 1994

Related U.S. Application Data

[63] Continuation of Ser. No. 154,578, Nov. 19, 1993, abandoned, which is a continuation of Ser. No. 40,043, Mar. 30, 1993, abandoned.

[30] Foreign Application Priority Data

Apr. 6, 1992 [EP] European Pat. Off. ............ 92105902

[51] Int. Cl.⁶ ................................................. G01N 33/00
[52] U.S. Cl. ............................ 422/64; 422/63; 422/99; 422/103; 422/104; 436/45
[58] Field of Search ................................. 422/63, 64, 65, 422/66, 99, 103, 104; 436/45, 47

[56] References Cited

U.S. PATENT DOCUMENTS

| | | | |
|---|---|---|---|
| 3,680,967 | 8/1972 | Engelhardt | 422/64 X |
| 4,123,173 | 10/1978 | Bullock et al. | 422/64 X |
| 4,126,418 | 11/1978 | Krasnow | 422/64 |
| 4,256,696 | 3/1981 | Soodak | 422/64 X |
| 4,357,301 | 11/1982 | Cassaday et al. | 422/64 |
| 4,360,360 | 11/1982 | Chiknas | 422/64 X |
| 4,634,575 | 1/1987 | Kawakami et al. | 422/104 X |
| 4,676,952 | 6/1987 | Edelmann et al. | 422/72 |
| 4,695,430 | 9/1987 | Coville et al. | 422/65 |
| 4,785,407 | 11/1988 | Sakagami | 422/64 X |
| 4,956,148 | 9/1990 | Grandone | 422/64 |
| 5,098,661 | 3/1992 | Froehlich et al. | 422/104 X |
| 5,320,808 | 6/1994 | Holen et al. | 422/64 |
| 5,324,481 | 6/1994 | Dunn et al. | 422/64 |

FOREIGN PATENT DOCUMENTS 222466  2/1986  European Pat. Off. .

Primary Examiner—James C. Housel
Assistant Examiner—Maureen M. Wallenhorst
Attorney, Agent, or Firm—George M. Gould; George W. Johnston; John P. Parise

[57] ABSTRACT

A conveyor is useful for conveying cuvettes to one or more processing stations. The conveyor has a plate-shaped rotor magazine with a number of resilient retaining elements for releasably holding cuvettes along the periphery of the magazine. This allows the cuvettes to be inserted and removed by a simple linear motion. Preferably, the retaining elements are constructed to cover the openings in the cuvettes while they are being held along the periphery of the magazine.

3 Claims, 3 Drawing Sheets

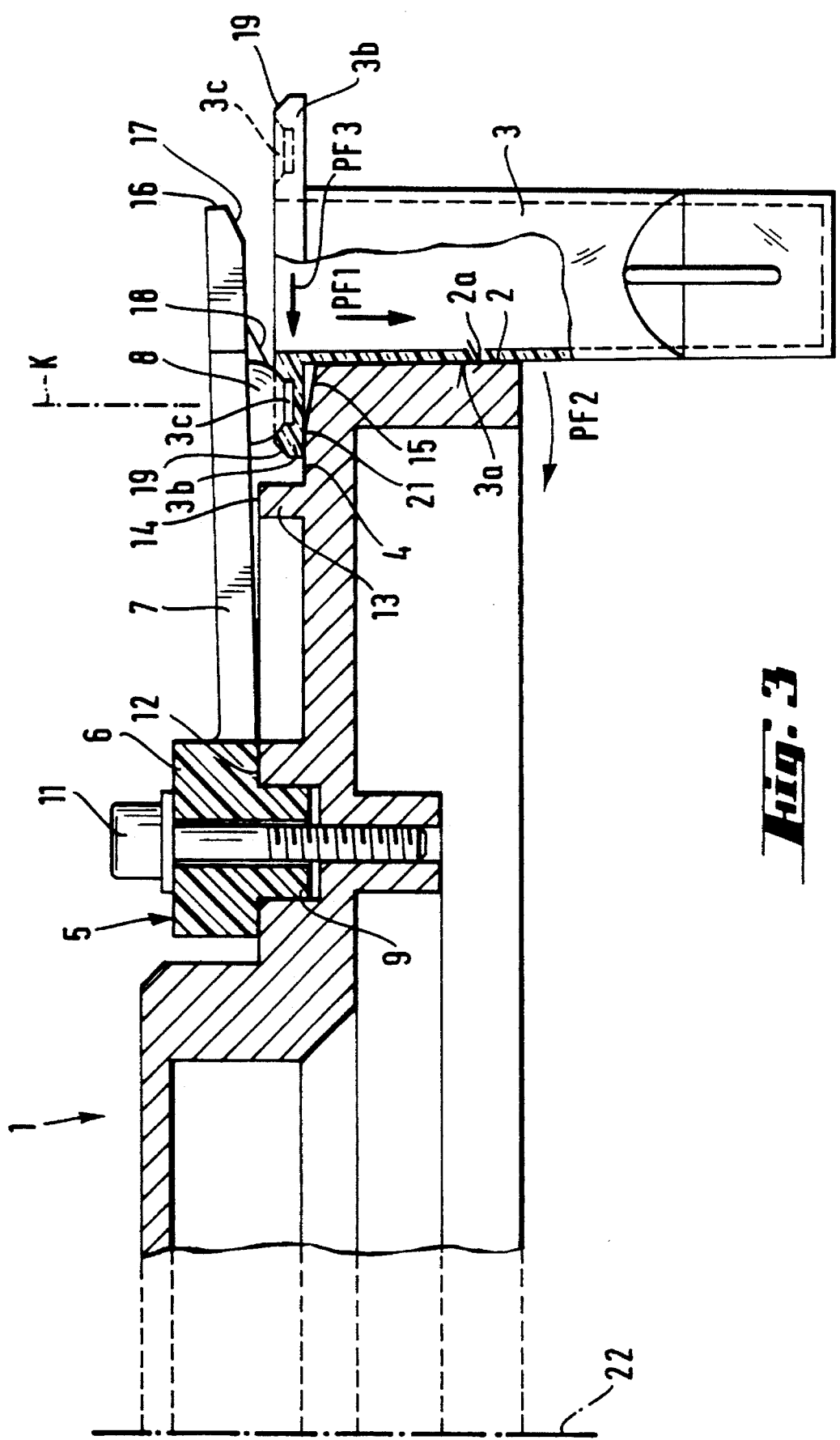

CUVETTE CONVEYOR

This is a continuation of application Ser. No. 08/154,578, filed Nov. 19, 1993, now abandoned which is a continuation of application Ser. No. 08/040,043, filed Mar. 30, 1993, now abandoned.

FIELD OF THE INVENTION

The invention relates to a device for chemical and biochemical analysis, more particularly to a conveyor for conveying cuvettes to a number of stations for processing the analytical samples in the cuvettes.

BACKGROUND OF THE INVENTION

Automatic analytical devices usually operate on the following principle: samples for analysis or parts of samples are placed in containers and then subjected to a series of processing steps such as adding (pipetting) reagents, mixing or incubation, and measurements of the reactions which have taken place are made a number of times during processing and/or once at the end of processing. The usual procedure is as follows: the containers holding the samples for analysis are placed in a fixed sequence on a conveyor and travel through various processing stations, or in the case of "batch processing", as is usual in the case of "centrifugal analytical devices", all sample containers are placed on a carrier (rotor) and subjected practically simultaneously to the processing steps and measurements. Analytical systems operating on these principles give good service in large clinics and analytical centers where large numbers of samples have to be processed.

In view of the variety of possible analyses today and the medical requirements, particularly in clinical chemistry, it has been found that the automatic analysers conventionally used for throughput of large quantities of samples are insufficiently flexible to provide analytical profiles (full random access) specifically adapted to individual patients or medical conditions, while still being able to handle a large number of samples from patients.

SUMMARY OF THE INVENTION

The aim of the invention is to provide an analytical system which meets these requirements in that a large number of analytical samples can be processed with very great flexibility with regard to the analytical profile obtained from the individual sample.

To this end according to the invention the conveyor contains a substantially disc-shaped rotor magazine having a periphery along which a number of cuvette-holding means are disposed. The cuvette holding means contain resilient holding elements which firmly secure the cuvettes to the rotor magazine but enable them to be removed in a radial direction with respect to the disc-shaped magazine.

BRIEF DESCRIPTION OF THE DRAWINGS

FIG. 3 is a larger-scale vertical section along line III—III in FIG. 1.

DETAILED DESCRIPTION OF THE INVENTION

Figure 1:
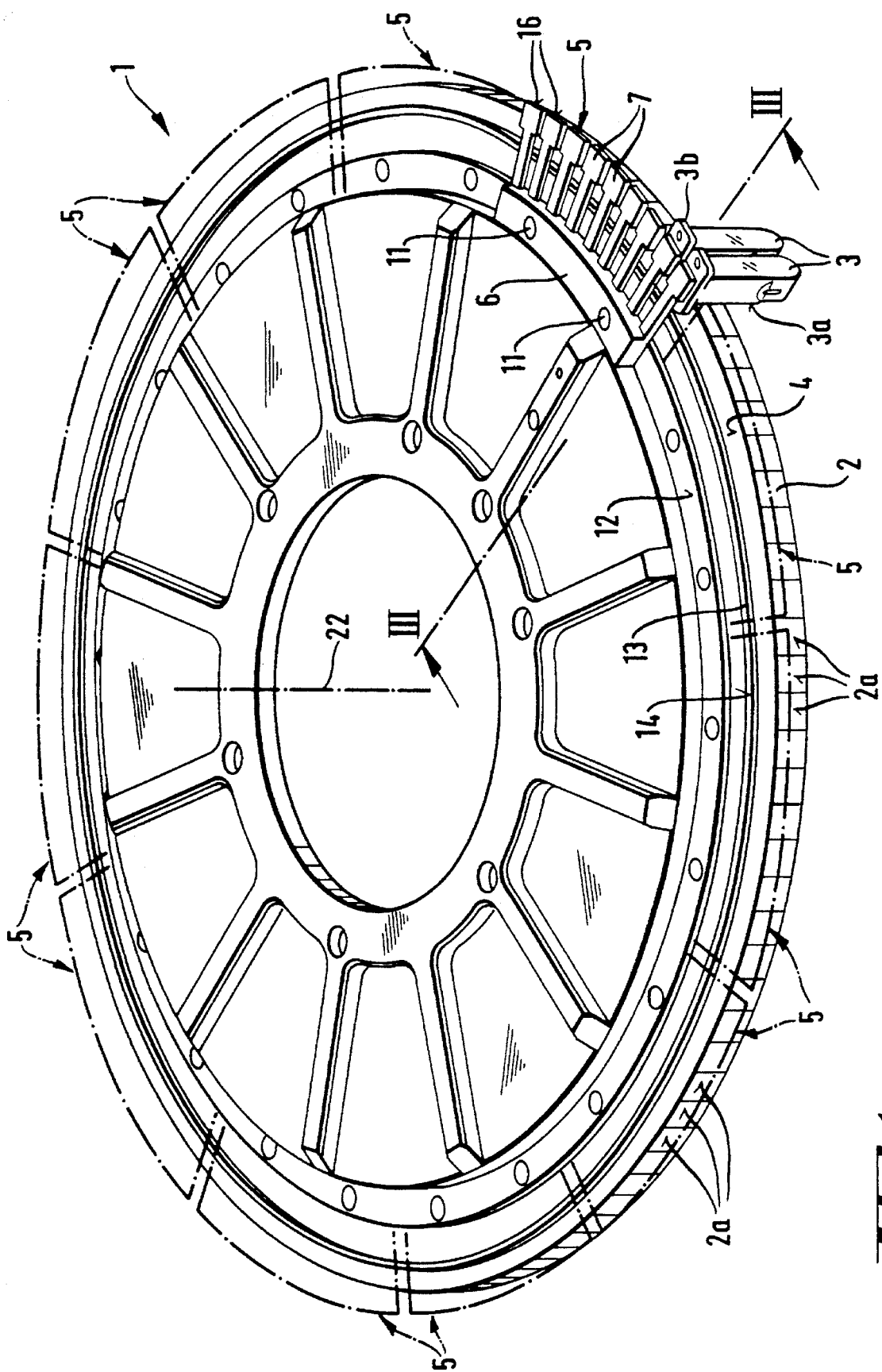
FIG. 1 shows a conveying and positioning device in the form of a rotor magazine in axonometric view, the retaining leaf springs and the cuvettes being shown only in part.

The invention pertains to a conveyor device in particular, to an automatic analytical apparatus having at least one processing station wherein a conveyor is provided for conveying a plurality of cuvettes to at least one processing station, wherein the cuvettes have a laterally extending flange. The conveyor includes a substantially disc-shaped magazine having an upper surface and defining an annular side surface which is substantially perpendicular to the upper surface. The conveyor also includes a plurality of retaining means disposed around the periphery of the magazine, each retaining means comprising a resilient holding member for securely and releasably holding the laterally extending flange of the cuvette between the upper surface of the magazine and the holding member.

The rotor magazine is not required to be circular. In a preferred embodiment, periphery 2 is a polygon. Its outer surface consists of 99 flat facets 2a. The flat surfaces of the facets 2a make it easier for the cuvettes to abut them, the outer cuvette walls 3a likewise being flat. Each facet, therefore, is a surface for a cuvette to rest against. The rotor magazine therefore may have space for any number of cuvettes, but in a preferred embodiment, has space for up to 99 cuvettes. Of course the number of spaces or cuvettes on the rotor magazine can be less than or greater than 99 in other embodiments.

On the outer edge of its surface, the rotor magazine has a narrow flat annular surface 4 which is substantially vertically adjacent the facetted outer wall. The annular surface serves as a table for supporting the two flanges 3b on the cuvettes. In a preferred embodiment, the top surface of each flange 3b contains a recess 3c for positive engagement of retaining means.

The cuvettes abut the facets and the flanges rest on the annular surface, thus defining the exact position of the cuvettes in the radial and vertical direction.

The following description relates to a preferred embodiment, and it will be apparent to one of skill in the art that other embodiments are possible without departing from the scope of the invention.

Figure 2:
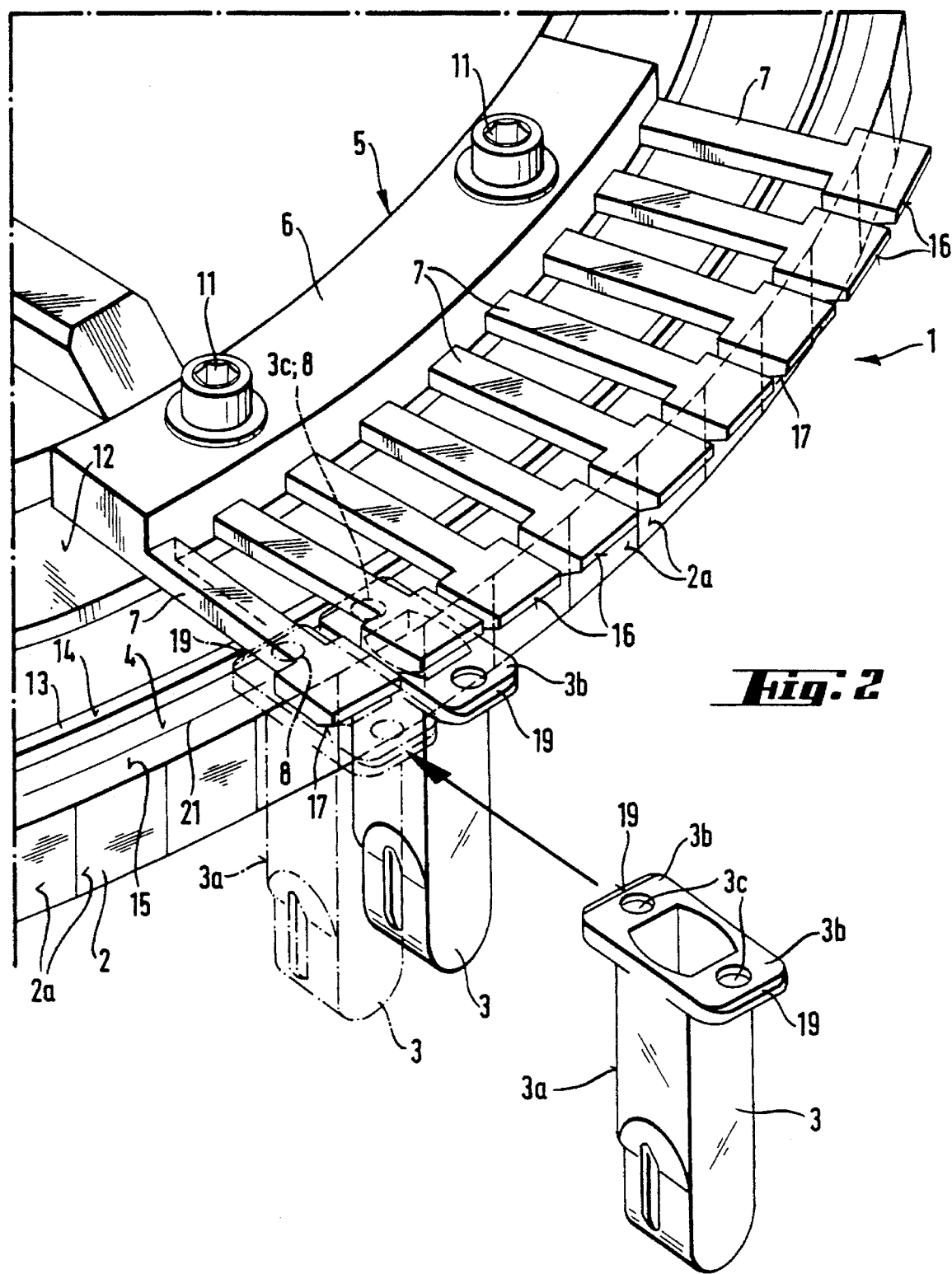
FIG. 2 is a larger-scale axonometric detail from FIG. 1.

The cuvettes are retained in this position by resilient retaining means 5, shown in detail in FIGS. 2 and 3. The retaining means 5 are likewise distributed round the entire rotor periphery. For simplicity and clarity, they are shown only by way of example at one place on the rotor. In a preferred embodiment, they comprise radial resilient tongues 7 secured at their radially inner ends to the carrier, whereas their radially outer ends abut the flanges 3b on the cuvettes.

In a further preferred embodiment, the tongues 7 are not individually secured to the carrier; instead, groups of nine tongues are secured at their radially inner ends by a transverse strip 6 to form a comb-Like element, which is secured by screws 11 to an annular surface 12 on the rotor magazine.

In a further embodiment, the annular surface 4 has an upwardly projecting, integrally moulded tongue-abutment strip 13, having a surface 14 on which the tongues 7 rest when in the inoperative state (when there are no cuvettes In the storage space).

The tongues 7 underneath are formed with lugs 8 which cooperate with the recesses 3c in the cuvette flanges 3b, so that each tongue 7 presses a cuvette flange 3b against the annular surface 4 and also presses the flat longitudinal side 3a of the cuvette against a flat facet 2a in the peripheral region 2 of the rotor magazine 1, thus exactly positioning the cuvette.

At their free ends, the tongues 7 widen to form a cover which covers the cuvettes while on the rotor magazine, thus largely preventing evaporation.

In order to insert the flange 3b of a cuvette 3, which is radially and horizontally moved on to the peripheral edge 2 of the rotor magazine 1, the annular surface 4 at the outer edge 2 of the rotor has a bevel 15 forming a slope for introducing the cuvette flange 3b. The free end 16 of the tongue has a bevel 17 for inserting a cuvette flange 3b which is correspondingly bevelled at 19.

To help in guiding the tongue 7 by means of the cuvette flange 3b, an ascending run-up slope 18 is provided on the underside of tongue 7 on the spherical cap-shaped retaining lug 8.

The lug 8 is dimensioned so that tongue 7 is still under residual tension when the lug 8 has engaged in the recess 3c in the cuvette flange 3b.

The following three forces act on cuvette 3 via the tongue 7 or lug 8 and via the recess 3c in the flange 3b:

1. A vertically downward force in the direction of arrow PF 1;
2. A rotary force in the direction of arrow PF 2 and having a center of rotation 21 substantially in the transition region between the bevel 15 and the horizontal region of the table 4. The center of rotation 21 is offset inwards in the direction of the axis of rotation 22 of the rotor, relative to the vertical line of action K of tongue 7.
3. A radially horizontal and inwardly directed force in the direction of the axis of rotation 22 of the rotor as per arrow PF 3, as a result of the centering action of the retaining lug 8 in the recess 3c.

The centering action of lug 8 in recess 3c also results in exact positioning in the peripheral direction in accordance with the required angular division of the rotor magazine 1.

Consequently the cuvette flange 3b and the flat longitudinal side 3a of the cuvette rest tightly against the table 4 or against the flat peripheral facets 2a of the rotor magazine 1.

The cuvettes can be placed on or removed from the rotor magazine by simple radial motion with respect to the disc-shaped rotor magazine without lifting, lowering or rotation. The cuvettes can be inserted and removed by a device, details of which are given in the European Patent Publication No. 0 564 906, published Oct. 13, 1993 (see also co-pending U.S. patent application Ser. No. 08/188,341), to which reference is made hereby.

What is claimed is:

1. In an automatic analytical apparatus having (i) at least one processing station and (ii) a conveyor for conveying. a plurality of cuvettes each having a laterally extending flange, to the at least one processing station, wherein the improvement comprises the conveyor having:

(a) a substantially disc-shaped magazine having an upper surface and an annular side surface, the annular side surface being substantially perpendicular to the upper surface and configured and dimensioned to provide a plurality of cuvette spaces, each cuvette space being positioned to receive a cuvette introduced radially with respect to the magazine so that each cuvette rests adjacent the annular side surface; and (b) a plurality of retaining means disposed peripherally on the upper surface of the magazine, each retaining means comprising a resilient holding member for securely and releasably holding the laterally extending flange of a cuvette between the upper surface of the magazine and the holding member when the cuvette is adjacent a cuvette space.

2. The automatic analytical apparatus of claim 1, wherein the improvement further comprises each cuvette having a recess in its laterally extending flange and each resilient holding member is an elongated member having a radially outer end and an radially inner end relative to the magazine, the radially outer end having a lug and the radially inner end being secured to the magazine so that the lug on the radially outer end releasably engages the recess in the cuvette flange of a cuvette adjacent a cuvette space.

3. The automatic analytical apparatus of claim 2, wherein each resilient holding member has a radially outer lower edge which has a surface that slopes relative to a plane parallel to the upper surface of the disc-shaped magazine.

* * * * *